(12) United States Patent
Mutel et al.

(10) Patent No.: US 6,596,731 B2
(45) Date of Patent: Jul. 22, 2003

(54) SUBSTITUTED IMIDAZO[1,2-A] PYRIDINE DERIVATIVES

(75) Inventors: Vincent Mutel, Brunstatt (FR); Jens-Uwe Peters, Grenzach-Wyhlen (DE); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/093,790

(22) Filed: Mar. 8, 2002

(65) Prior Publication Data

US 2002/0188128 A1 Dec. 12, 2002

(30) Foreign Application Priority Data

Mar. 27, 2001 (EP) .............................. 01107562

(51) Int. Cl.[7] ..................... A61K 31/437; C07D 471/04
(52) U.S. Cl. ....................... 514/300; 546/121
(58) Field of Search ................. 546/122, 121; 514/300

(56) References Cited

U.S. PATENT DOCUMENTS 3,701,780 A   10/1972   Fisher

FOREIGN PATENT DOCUMENTS

| | | |
|---|---|---|
| CH | 590 862 | 8/1977 |
| EP | 050 563 | 4/1982 |
| EP | 092 458 | 10/1983 |
| EP | 092 459 | 10/1983 |
| EP | 172 096 | 2/1986 |
| EP | 185 345 | 6/1986 |
| EP | 234 970 | 9/1987 |
| EP | 251 859 | 1/1988 |
| EP | 267 111 | 5/1988 |
| FR | 2 581 646 | 11/1986 |
| JP | 50-140477 | 11/1975 |
| JP | 51-004194 | 1/1976 |
| JP | 51-125095 | 11/1976 |
| JP | 11-116481 | 4/1999 |
| WO | WO 91/19497 | 12/1991 |
| WO | WO 98/39342 | 9/1998 |
| WO | WO 00/08021 | 2/2000 |
| WO | WO 01/74815 | 10/2001 |

OTHER PUBLICATIONS

Schlaeger et al., Cytotechnology, 30, pp. 71–83 (1999).
Möhler et al., Nature, 294, pp. 763–765 (1981).
Katritzky et al., J. Org. Chem., 65, pp. 9201–9205 (2000).
Sundberg et al., J. Heterocyclic Chem., 25, pp. 129–137 (1988).
Andreani et al., Eur. J. Med. Chem., 29, pp. 339–342 (1994).
Habermann et al., J. Chem. Soc., Perkin Trans. 1, pp. 2425–2427 (1999).
Arbilla et al., Eur. J. Pharmacol., 130, pp. 257–263 (1986).
Maruyama et al., Arzneim.–Forsch, 31(7), pp. 1111–1118 (1981).
Crestani et al., Br. J. Pharmacol, 131, pp. 1251–1254 (2000).
Buu–Hoï et al., J. Org. Chem., 19, pp. 1370–1374 (1954).
Buu–Hoï et al., Recl. Trav. Chim. Pays–Bas, 68, pp. 441–472 (1949).
Möhler et al., J. Neurochemistry, 37, pp. 714–722 (1981).
Tomoda et al., Bull. Chem. Soc. Jpn., 72, pp. 1327–1334 (1999).
Loiseau et al., Eur. J. Med. Chem., 22, pp. 457–462 (1987).
Kempter et al., J. Prakt. Chem, 313, pp. 977–985 (1971).
Pentimalli et al., Boll. Sci. Fac. Chim. Ind. Bologna, 24, pp. 205–214 (1966).
Khim.–Farm. Zh., 4, pp. 20–26 (1970).
Barlin, Gordon B., Journal of Heterocyclic Chemistry, 35(5), pp. 1205–1217 (1998).
Almirante, Luigi et al., J. Med. Chem, 8(3), pp. 305–12 (1965).

*Primary Examiner*—Charanjit S. Aulakh
(74) *Attorney, Agent, or Firm*—George W. Johnston; Patricia S. Rocha-Tramaloni; Lyman H. Smith

(57) ABSTRACT

The present invention is a series of novel compounds of formula I and a method of treatment or prevention of a mGluR5 receptor mediated disease by administering an therapeutically effective amount of a compound formula

I

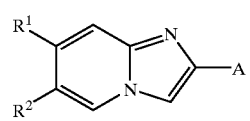

wherein $R^1$ and $R^2$ are selected from hydrogen, $(C_{1-6})$-alkyl, halogen, hydroxy, $(C_{1-6})$-alkoxy and A is defined the description, or a pharmaceutically acceptable salt thereof.

7 Claims, No Drawings

SUBSTITUTED IMIDAZO[1,2-A] PYRIDINE DERIVATIVES

BACKGROUND

The synthesis of some imidazo[1,2-a]pyridine derivatives is described in *Recl. Trav. Chim. Pays-Bas* 1949, 68, 441–470, in *J. Org. Chem.* 1954, 19, 1370–1374, in *J. Heterocyclic Chem.* 1988, 25, 129–137, in International patent application WO 00/08021 or in *J. Org. Chem.* 2000, 65, 9201–9205. According to *J. Prakt. Chem* 1971, 313, 977–985, imidazo[1,2-a]-pyridines bearing a benzothienyl, thienyl or benzofuranyl group have been prepared by condensation of α-haloketones or α-hydroxyketones with amidines. The synthesis and antimicrobial action of furyl derivatives of imidazo[1,2-a]pyrimidine is reported in *Khim.-Farm. Zh.* 1970, 4, 20–26.

Different uses have been described for imidazo[1,2-a] pyridine derivatives. The preparation of 2-[p-(dimethylamino)phenyl]-imidazo[1,2-a]pyridine as an azo dye and its evaluation as disperse dye on synthetic fibers, cellulose acetate, and cotton is described in *Boll. Sci. Fac. Chim. Ind. Bologna* 1966, 24, 205–214. Fluorescent properties of imidazo[1,2-a]-pyridine-based compounds are described in *Bull. Chem. Soc. Jpn.* 1999, 72(6), 1327–1334. Japanese patent applications JP 50-140477, JP 51-004194 and JP 51-125095 report the analgesic, antiinflammatory, antipyretic, and local anesthetic activities of certain phenyl-imidazo[1,2-a]pyridines wherein the phenyl ring is substituted by $-CR^1R^2COOH$, $-CR^1R^2COOR$, $-CR^1R^2CONH_2$, $-CR^1R^2CSNH_2$, $-CR^1R^2CN$, $-CO_2-(CH_2)_{1-4}-NR^3R^4$ or $-CH_2OH$ and R, $R^1$, $R^2$, $R^3$ and $R^4$ are hydrogen or alkyl. According to *Arzneim.-Forsch.* 1981, 31(7), 1111–1118, the most preferred compound thereof, viz. 4-imidazo[1,2-a]pyridin-2-yl-α-methyl-benzeneacetic acid (miroprofen) is effective in suppressing pain responses and acute inflammation accompanied by increased vascular permeability. The use of imidazo[1,2-a] pyridines substituted at the 2 and 6 positions as anthelmintic and fungicidal agents is disclosed in U.S. Pat. No. 3,701,780. Isothiocyanato derivatives like 2-(4-isothiocyanato-phenyl) -6-methyl-imidazo[1,2-a]pyridine are described as antihelmintics in Swiss patent No. CH 590 862.

The use of imidazo[1,2-a]pyridine derivatives as inhibitors for STAT6 6 transcription factor activation and IL 4 antagonists for treatment of allergic, autoimmune, parasital, viral, and bacterial diseases, tumors, host-vs. graft syndrome, systemic lupus erythematosus, and AIDS is disclosed in Japanese patent application No. JP 11-116481.

According to *Eur. J. Med. Chem.* 1994, 29(5), 339–342, aryl- or pyridyl-substituted fused imidazoles such as 2-(4-pyridinyl)-imidazo[1,2-a]pyridine, possess cardiotonic activity. N-(4-imidazo[1,2-a]pyridin-2-yl-phenyl)-methanesulfonamide has been prepared and is reported as an antithrombotic and cardiovascular agent in European patent application EP 0 185 345. According to *Eur. J. Med. Chem.* 1987, 22(5), 457–462, certain imidazo[1,2-a]pyrimidines, e.g. 2-(2-furanyl)-imidazo[1,2-a]pyridine, were tested for bronchodilator activity and for inhibition of a cardiac phosphodiesterase. Phosphonic acid derivatives of imidazo[1,2-a]pyridines, e.g. [5-(6-chloroimidazo[1,2-a]pyridin-2-yl)-2-furanyl]-phosphonic acid, are described as human liver fructose-1,6-bisphosphatase inhibitors in International patent application WO 98/39342.

N,N,6-trimethyl-2-(4-methylphenyl)-imidazo[1,2-a] pyridine-3-acetamide (Zolpidem) and its use as anticonvulsant and hypnotic was first disclosed in European patent application EP 0 050 563. Further imidazo[1,2-a]pyridine derivatives with anticonvulsant, hypnotic and anxiolytic activity are also described in the patent applications EP 0 092 458, EP 0 092 459, EP 0 172 096, FR 25 81 646, EP 0 234 970, EP 0 251 859 and EP 0 267 111. *Eur. J. Pharmacol.* 1986, 130(3), 257–263, reports that Zolpidem possesses agonist properties at central benzodiazepine receptors and according to *Br. J. Pharmacol.* 2000, 131(7), 1251–1254 the mechanism of action of Zolpidem in vivo is based on its high affinity to the α1-GABAA receptor benzodiazepine site.

SUMMARY

The present invention is a method of treating a disease responsive to mediating the mGluR5 receptor by administering, to a person in need of such treatment, a therapeutically effective amount of a compound of formula

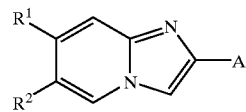

I wherein $R^1$ is selected from the group consisting of hydrogen, $(C_{1-6})$-alkyl, halogen, hydroxy and $(C_{1-6})$-alkoxy;

$R^2$ is selected from the group consisting of hydrogen, $(C_{1-6})$-alkyl, halogen, hydroxy and $(C_{1-6})$-alkoxy; and A is unsubstituted aryl or aryl substituted with at least one substituent selected from the group consisting of $(C_{1-6})$-alkyl, halogen, halogen-$(C_{1-6})$-alkyl, hydroxy, $(C_{1-6})$-alkoxy, benzyloxy, amino, $(C_{1-6})$-alkylamino, di-$(C_{1-6})$-alkyl-amino, arylamino, diarylamino and nitro, or is unsubstituted heteroaryl or heteroaryl substituted with at least one substituent selected from the group consisting of $(C_{1-6})$-alkyl, halogen, halogen-$(C_{1-6})$-alkyl, hydroxy, $(C_{1-6})$-alkoxy, benzyloxy, amino, $(C_{1-6})$-alkylamino, di-$(C_{1-6})$-alkyl-amino, arylamino, diarylamino and nitro or signifies the group

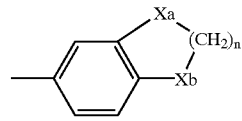

wherein $X_a$, $X_b$ are, independently from each other, selected from the group consisting of $CH_2-$ and $-O-$; and n is 1 or 2;

or a pharmaceutically acceptable salt thereof.

It has now surprisingly been found that the compounds of formula I are metabotropic glutamate receptor antagonists. Compounds of formula I are distinguished by having valuable therapeutic properties. These compounds can be used in the treatment or prevention of mGluR5 receptor mediated disorders.

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR receptors are known and some of these even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and pain. Selective mGluR5 antagonists are especially useful for the treatment of anxiety and pain.

Objects of the present invention are the use of compounds of formula I and their pharmaceutically acceptable salts for the manufacture of pharmaceutical compositions for the treatment or prevention of mGluR5 receptor mediated disorders, such as acute and/or chronic neurological disorders, cognitive disorders and memory deficits such as Alzheimer's disease, senile dementia, Parkinson's disease, ischemia, Huntington's chorea, amyotrophic lateral sclerosis and multiple sclerosis, psychiatric diseases such as psychosis, epilepsy, schizophrenia, anxiety and depression as well as chronic and acute pain.

DETAILED DESCRIPTION

The following definitions of general terms used in the present description apply irrespective of whether the terms in question appear alone or in combination. The term "$(C_{1-6})$-alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "halogen" denotes fluorine, chlorine, bromine and iodine.

The term "halogen-$(C_{1-6})$-alkyl" denotes $(C_{1-6})$-alkyl, wherein the hydrogen atoms are replaced by one or more halogen atoms.

The term "$(C_{1-6})$-alkoxy" denotes a $(C_{1-6})$-alkyl group as defined hereinbefore, which is bound via an oxygen atom, e.g. methoxy, ethoxy, n-propoxy, isopropoxy, n-butoxy and the like.

"Aryl" represents an aromatic carbocyclic group consisting of one individual ring, or one or more fused rings in which at least one ring is aromatic in nature. Preferred aryl groups are phenyl or naphthyl.

The term "heteroaryl" refers to an aromatic 5- or 6-membered ring containing one or more heteroatoms selected from nitrogen, oxygen or sulphur, or to a bicyclic aromatic group comprising two 5- or 6-membered rings, in which one or both rings can contain one or more heteroatoms selected from nitrogen) oxygen or sulphur. Examples of such heteroaryl groups are furyl, pyrrolyl, thienyl (thiophenyl), 1H-imidazolyl, 2H-imidazolyl, 4H-imidazolyl, 1H-pyrazolyl, 3H-pyrazolyl, 4H-pyrazolyl, 1,2-oxazolyl, 1,3-oxazolyl, [1,2,4]triazolyl, [1,2,3]triazolyl, [1,2,4]oxadiazolyl, [1,3,4]oxadiazolyl, [1,2)3]oxadiazolyl, tetrazolyl, [1,2,3,4]oxatriazolyl, [1,2,3,5]oxatriazolyl, 1,3-thiazolyl, 1,2-thiazolyl, pentazolyl, pyridyl, pyrazinyl, pyrimidinyl, pyridazinyl, benzofuryl (benzofuranyl), benzothienyl (benzothiophenyl), benzimidazolyl, benzo[1,4]dioxinyl, benzoxazolyl, benzothiazolyl, indolyl, isoindolyl, quinolyl, isoquinolyl and their dihydro derivatives.

Preferred heteroaryl groups are thienyl, benzofuryl or benzothienyl.

The term "$(C_{1-6})$-alkylamino" denotes a straight-chain or branched alkyl chain having from one to six carbon atoms attached to an amino group. Examples of such $(C_{1-6})$-alkylamino groups are methylamino, ethylamino, isopropylamino and the like. "Di-$(C_{1-6})$-alkylamino" represents two straight-chain or branched dialkyl chains having from one to six carbon atoms attached to an amino group. Examples of such di-$(C_{1-6})$-alkylamino groups are dimethylamino, ethylmethylamino and the like. "Arylamino" denotes an aryl group as defined above attached to an amino group. A phenylamino group is an example of such a group.

The term "pharmaceutically acceptable salt" refers to any salt derived from an inorganic or organic acid or base known to one skilled in the art as usable in a pharmaceutical preparation.

Preferred compounds of formula I for the above mentioned method of treatment are those, in which A is unsubstituted aryl or aryl substituted with at least one substituent selected from the group consisting of $(C_{1-6})$-alkyl, halogen, halogen-$(C_{1-6})$-alkyl, hydroxy, $(C_{1-6})$-alkoxy, benzyloxy, amino, $(C_{1-6})$-alkylamino, di-$(C_{1-6})$-alkyl-amino, arylamino, diarylamino and nitro.

Especially preferred for the above mentioned method of treatment are those compounds of formula I, in which A is unsubstituted phenyl or phenyl substituted with one or more substituents selected from the group consisting of $(C_{1-6})$-alkyl, halogen, halogen-$(C_{1-6})$-alkyl, hydroxy, $(C_{1-6})$-alkoxy, benzyloxy, amino, $(C_{1-6})$-alkylamino, di-$(C_{1-6})$-alkylamino, arylamino, diarylamino or nitro.

Even more preferred for the above mentioned method of treatment are compounds of formula I, in which A signifies phenyl substituted with one substituent selected from the group consisting of $(C_{1-6})$-alkyl, halogen, halogen-$(C_{1-6})$-alkyl, hydroxy, $(C_{1-6})$-alkoxy, benzyloxy, amino, $(C_{1-6})$-alkylamino, di-$(C_{1-6})$-alkyl-amino, arylamino, diarylamino or nitro. The following are examples of these more preferred compounds:

2-(3-bromo-phenyl)-imidazo[1,2-a]pyridine,
2-(3-iodo-phenyl)-imidazo[1,2-a]pyridine, 2-(3-chloro-phenyl)-imidazo[1,2-a]pyridine,
2-(3-methyl-phenyl)-imidazo[1,2-a]pyridine,
2-(3-trifluoromethyl-phenyl)-imidazo[1,2-a] pyridine,
2-(3-fluoro-phenyl)-imidazo[1,2-a]pyridine,
7-methyl-2-phenyl-imidazo[1,2-a]pyridine,
2-(4-methyl-phenyl)-imidazo[1,2-a]pyridine,
2-(3-methoxy-phenyl)-imidazo[1,2-a]pyridine,
6-methyl-2-(4-methyl-phenyl)-imidazo[1,2-a]pyridine, and
2-(3-nitro-phenyl)-imidazo[1,2-a]pyridine.

Further preferred are those compounds of formula I for the above mentioned method of treatment, in which A is phenyl substituted with at least two substituents selected from the group consisting of $(C_{1-6})$-alkyl, halogen, halogen-$(C_{1-6})$-alkyl, hydroxy, $(C_{1-6})$-alkoxy, benzyloxy, amino, $(C_{1-6})$-alkylamino, di-$(C_{1-6})$-alkylamino, arylamino, diarylamino and nitro.

Examples of these further preferred compounds are
7-chloro-2-(3,4-dimethyl-phenyl)-imidazo[1,2-a]pyridine,
2-(3,4-dimethoxy-phenyl)-7-methyl-imidazo[1,2-a]pyridine,
2-(3,4-dimethoxy-phenyl)-imidazo[1,2-a]pyridine,
2-(3,4-dimethyl-phenyl)-7-methoxy-imidazo[1,2-a]pyridine,
2-(3,4-dimethoxy-phenyl)-7-methoxy-imidazo[1,2-a]pyridine,
2-(3,4-dimethyl-phenyl)-imidazo[1,2-a]pyridine hydrochloride,
2-(3,4-dimethyl-phenyl)-7-methyl-imidazo[1,2-a]pyridine,
2-(3-bromo-4-fluoro-phenyl)-imidazo[1,2-a]pyridine,
2-(4-benzyloxy-3-methoxy-phenyl)-imidazo[1,2-a]pyridine,
2-(3,4-dimethyl-phenyl)-7-ethyl-imidazo[1,2-a]pyridine, or
2-(3,4-dimethoxy-phenyl)-6-methyl-imidazo[1,2-a]pyridine.

Also preferred for the above mentioned method of treatment are compounds of formula I, in which A is unsubstituted heteroaryl or heteroaryl substituted with at least one substituent selected from the group consisting of $(C_{1-6})$-alkyl, halogen, halogen-$(C_{1-6})$-alkyl, hydroxy, $(C_{1-6})$-alkoxy, benzyloxy, amino, $(C_{1-6})$-alkylamino, di-$(C_{1-6})$-alkylamino, arylamino, diarylamino and nitro.

The following are examples of these also preferred compounds:
2-benzofuran-2-yl-imidazo[1,2-a]pyridine,
2-benzo[b]thiophen-3-yl-imidazo[1,2-a]pyridine,
2-(5-methyl-thiophen-2-yl)-imidazo[1,2-a]pyridine, and
2-(2,5-dimethyl-thiophen-3-yl)-imidazo[1,2-a]pyridine.

Preferred compounds of formula I for the above mentioned method of treatment are also those, in which A is the group

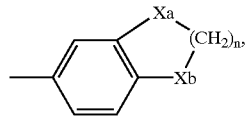

wherein $X_a, X_b$ are, independently from each other, selected from the group consisting of —CH$_2$— and —O—; and n is 1 or 2. The following are examples of these preferred compounds:
2-indan-5-yl-imidazo[1,2-a]pyridine,
2-(2,3-dihydro-benzofuran-5-yl)-imidazo[1,2-a]pyridine, and
2-(2,3-dihydro-benzo[1,4]dioxin-6-yl)-imidazo[1,2-a]pyridine.

The present invention is also directed to the following novel compounds of formula I:

7-chloro-2-(3,4-dimethyl-phenyl)-imidazo[1,2-a]pyridine,
2-(3,4-dimethoxy-phenyl)-imidazo[1,2-a]pyridine,
2-(3,4-dimethyl-phenyl)-7-methoxy-imidazo[1,2-a]pyridine,
2-(3,4-dimethoxy-phenyl)-7-methoxy-imidazo[1,2-a]pyridine,
2-(3,4-dimethyl-phenyl)-7-methyl-imidazo[1,2-a]pyridine,
2-(3-bromo-4-fluoro-phenyl)-imidazo[1,2-a]pyridine,
2-(4-benzyloxy-3-methoxy-phenyl)-imidazo[1,2-a]pyridine,
2-indan-5-yl-imidazo[1,2-a]pyridine,
2-(3-bromo-phenyl)-imidazo[1,2-a]pyridine,
2-(3-iodo-phenyl)-imidazo[1,2-a]pyridine,
2-(3-methyl-phenyl)-imidazo[1,2-a]pyridine,
2-benzo[b]thiophen-3-yl-imidazo[1,2-a]pyridine,
2-(3-trifluoromethyl-phenyl)-imidazo[1,2-a]pyridine,
2-(2,3-dihydro-benzofuran-5-yl)-imidazo[1,2-a]pyridine,
2-(3-fluoro-phenyl)-imidazo[1,2-a]pyridine,
2-(3,4-dimethyl-phenyl)-7-ethyl-imidazo[1,2-a]pyridine,
2-(5-methyl-thiophen-2-yl)-imidazo[1,2-a]pyridine,
2-(2,5-dimethyl-thiophen-3-yl)-imidazo[1,2-a]pyridine, and
2-(3,4-dimethoxy-phenyl)-6-methyl-imidazo[1,2-a]pyridine.

The present invention also includes pharmaceutical compositions containing a therapeutically effective amount of one or more of these novel compounds, namely 7-chloro-2-(3,4-dimethyl-phenyl)-imidazo[1,2-a]pyridine, 2-(3,4-dimethoxy-phenyl)-imidazo[1,2-a]pyridine, 2-(3,4-dimethyl-phenyl)-7-methoxy-imidazo[1,2-a]pyridine, 2-(3,4-dimethoxy-phenyl)-7-methoxy-imidazo[1,2-a]pyridine, 2-(3,4-dimethyl-phenyl)-7-methyl-imidazo[1,2-a]pyridine, 2-(3-bromo-4-fluoro-phenyl)-imidazo[1,2-a]pyridine, 2-(4-benzyloxy-3-methoxy-phenyl)-imidazo[1,2-a]pyridine, 2-indan-5-yl-imidazo[1,2-a]pyridine, 2-(3-bromo-phenyl)-imidazo[1,2-a]pyridine, 2-(3-iodo-phenyl)-imidazo[1,2-a]pyridine, 2-(3-methyl-phenyl)-imidazo[1,2-a]pyridine, 2-benzo[b]thiophen-3-yl-imidazo[1,2-a]pyridine, 2-(3-trifluoromethyl-phenyl)-imidazo[1,2-a]pyridine, 2-(2,3-dihydro-benzofuran-5-yl)-imidazo[1,2-a]pyridine, 2-(3-fluoro-phenyl)-imidazo[1,2-a]pyridine, 2-(3,4-dimethyl-phenyl)-7-ethyl-imidazo[1,2-a]pyridine, 2-(5-methyl-thiophen-2-yl)-imidazo[1,2-a]pyridine, 2-(2,5-dimethyl-thiophen-3-yl)-imidazo[1,2-a]pyridine, or 2-(3,4-dimethoxy-phenyl)-6-methyl-imidazo[1,2-a]pyridine, and a pharmaceutically acceptable carrier.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

The compounds of formula I or pharmaceutically acceptable salts thereof are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds of the present invention was tested using the following methods:

cDNA encoding rat mGlu 5a receptor was transiently transfected into EBNA cells using a procedure described by E. -J. Schlaeger and K. Christensen (Transient gene expression in mammalian cells grown in serum-free suspension culture, *Cytotechnology* 1999, 30, 71–83). $[Ca^{2+}]i$ measurements were performed on mGlu 5a transfected EBNA cells after incubation of the cells with Fluo 3-AM (obtainable by FLUKA, 0.5 $\mu$M final concentration) for 1 hour at 37° C. followed by 4 washes with assay buffer (DMEM supplemented with Hank's salt and 20 mM HEPES. $[Ca^{2+}]i$ measurements were done using a fluorometric imaging plate reader (FLIPR, Molecular Devices Corporation, La Jolla, Calif., USA). When compounds were evaluated as antagonists they were tested against 10 $\mu$M glutamate as agonist.

The inhibition (antagonists) curves were fitted with a four parameter logistic equation giving $IC_{50}$, and Hill coefficient using the iterative non linear curve fitting software Origin (Microcal Software Inc., Northampton, Mass., USA).

The compounds of the present invention are mGluR 5a receptor antagonists. In Table I the activities of compounds of formula I as measured in the assay described above are shown:

TABLE I

| Ex. | Activity [$\mu$M] |
|---|---|
| 1 | 0.1 |
| 2 | 1.88 |
| 3 | 6.8 |
| 4 | 0.14 |
| 5 | 3.3 |
| 6 | 0.037 |
| 7 | 0.28 |
| 8 | 0.69 |
| 9 | 0.83 |
| 10 | 0.93 |
| 11 | 0.95 |
| 12 | 0.97 |
| 13 | 1.23 |
| 14 | 1.55 |
| 15 | 1.66 |
| 16 | 2.76 |
| 17 | 2.79 |
| 18 | 2.86 |
| 19 | 3.41 |
| 20 | 3.64 |
| 21 | 6.13 |
| 22 | 7.5 |
| 23 | 8.77 |
| 24 | 0.58 |
| 25 | 1.65 |
| 26 | 8.3 |
| 27 | 0.99 |
| 28 | 10 |
| 29 | 10 |

The affinity of compounds of formula I to the central benzodiazepine receptors in vitro was also tested using standard methods as for example described in *Nature* 1981, 294, 763–765 and *J. Neurochemistry* 1981, 37, 714–722. According to these methods, the inhibition of the binding of tritiated flumazenil to the specific benzodiazepine receptors in the cortex of rats by the respective test substances is determined and the inhibition dissociation constant (Ki) of each test compound is determined according to the method of Cheng & Prusoff (1973). 2-(3,4-Dimethyl-phenyl)-imidazo[1,2-a]pyridine hydrochloride was tested according to this method and showed a pKi (negative logarithm of the Ki) of 5.2, i.e. the compound does not possess good affinity towards the benzodiazepine receptors. The fact that the compounds of formula I of the present invention do not possess good affinity to benzodiazepine receptors is surprising when the results for the cited reference presented above (in paragraph [0005]) for N,N,6-trimethyl-2-(4-methylphenyl)-imidazo[1,2-a]pyridine-3-acetamide are considered. The compound referenced in paragraph [0005] possesses agonist properties at central benzodiazepine receptors, but does not possess the affinity toward the mGluR5 receptor that is seen with the compounds of formula 1 of the present invention.

The compounds of formula I and pharmaceutically acceptable salts thereof can be used in the form of pharmaceutical compositions The pharmaceutical compositions can be administered orally, e.g. in the form of tablets, coated tablets, dragées, hard and soft gelatine capsules, solutions, emulsions or suspensions. The administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a effective amount of compound of formula I or pharmaceutically acceptable salts thereof and a therapeutically inert carrier are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the therapeutically effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The compounds of formula I and pharmaceutically acceptable salts thereof can be prepared by methods well known to those of ordinary skill in the art. For example, compounds of formula I can be obtained by reacting a compound of the formula

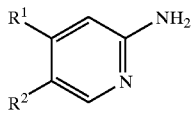

II with an α-bromo ketone of formula

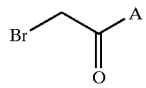

III wherein $R^1$, $R^2$ and A are as defined before, and if desired, converting a compound of formula I into a pharmaceutically acceptable salt.

This reaction is for example described in *J. Org. Chem.* 1954, 19, 1370–1374 or in *J. Heterocyclic Chem.* 1988, 25, 129–137. The cyclocondensation of 2-amino pyridines with α-bromo ketones is carried out in a polar solvent like ethanol and heated under reflux conditions for several hours or, alternatively, the reactants are dissolved in a solvent like acetone at room temperature.

The preparation of compounds of formula II is well known to those skilled in the art and some of the compounds of formula II are commercially available. Reviews for the synthesis of 2-aminopyridines can be found in M. T. Leffler, *Organic Reactions*, Vol. 1, Ed. R. Adams, J. Wiley and Sons, NY, 1942, Ch. 4, pp. 91–104, or in A. S. Tomcufcik, L. N. Starker, *The Chemistry of Heterocyclic Compounds, Pyridine and its Derivatives*, Part 3, Ed. E. Klingsberg, Interscience, NY, 1962, Ch. IX, pp. 1–177, or in E. F. V. Scriven, *Comprehensive Heterocyclic Chemistry*, Vol. 2, Part 2A, Eds. A. J. Boulton and A. McKillop, Pergamon Press, NY, 1984, Ch. 2.05, pp. 165–314. For instance, these compounds can be prepared by the Chichibabin reaction involving the reaction of a substituted pyridine derivative with sodium amide or sodium amide in the presence of a substituted amine to yield a 2-aminopyridine derivative of formula II.

The compounds of formula III are also commercially available or can be easily prepared by the method as described in *J. Chem. Soc., Perkin Trans.* 1, 1999, 2425–2427. For example, 2-bromo-1-(3-bromo-4-fluoro-phenyl)-ethanone, 1-(4-benzyloxy-3-methoxy-phenyl)-2-bromo-ethanone, 2-bromo-1-indan-5-yl-ethanone, 2-iodo-1-(3-bromo-phenyl)-ethanone, 2-bromo-1-m-tolyl-ethanone, 2-bromo-1-(3-trifluoromethyl-phenyl)-ethanone, 2-bromo-1-(2,3-dihydro-benzofuran-5-yl)-ethanone, 2-bromo-1-(3,4-dimethyl-phenyl)-ethanone, 2-bromo-1-(5-methyl-thiophen-2-yl)-ethanone, 2-bromo-1-(3-methoxy-phenyl)-propan-1-one, 2-bromo-1-(2,5-dimethyl-thiophen-3-yl)-ethanone, 2-bromo-1-(3,4-dimethoxy-phenyl)-ethanone, 2-bromo-1-(4-morpholin-4-yl-3-nitro-phenyl)-ethanone and 2-bromo-1-(3,4-dimethyl-phenyl)-hexan-1-one are obtained in analogy to this method by α-bromination of the appropriate commercially available acetophenones using polymer-supported pyridinium bromide perbromide (PSPBP) in toluene at 10° C. (scheme 1).

Scheme 1

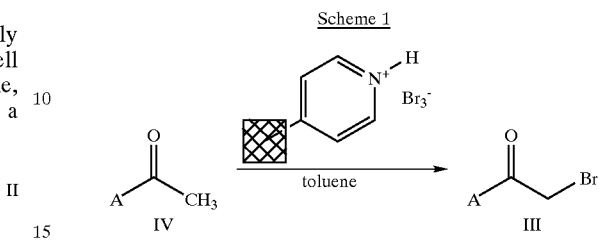

The preparation of compounds of formula I, especially of the novel compounds 7-chloro-2-(3,4-dimethyl-phenyl)-imidazo[1,2-a]pyridine, 2-(3,4-dimethoxy-phenyl)-imidazo[1,2-a]pyridine, 2-(3,4-dimethyl-phenyl)-7-methoxy-imidazo[1,2-a]pyridine, 2-(3,4-dimethoxy-phenyl)-7-methoxy-imidazo[1,2-a]pyridine, 2-(3,4-dimethyl-phenyl)-7-methyl-imidazo[1,2-a]pyridine, 2-(3-bromo-4-fluoro-phenyl)-imidazo[1,2-a]pyridine, 2-(4-benzyloxy-3-methoxy-phenyl)-imidazo[1,2-a]pyridine, 2-indan-5-yl-imidazo[1,2-a]pyridine, 2-(3-bromo-phenyl)-imidazo[1,2-a]pyridine, 2-(3-iodo-phenyl)-imidazo[1,2-a]pyridine, 2-(3-methyl-phenyl)-imidazo[1,2-a]pyridine, 2-benzo[b]thiophen-3-yl-imidazo[1,2-a]pyridine, 2-(3-trifluoromethyl-phenyl)-imidazo[1,2-a]pyridine, 2-(2,3-dihydro-benzofuran-5-yl)-imidazo[1,2-a]pyridine, 2-(3-fluoro-phenyl)-imidazo[1,2-a]pyridine, 2-(3,4-dimethyl-phenyl)-7-ethyl-imidazo[1,2-a]pyridine, 2-(5-methyl-thiophen-2-yl)-imidazo[1,2-a]pyridine, 2-(2,5-dimethyl-thiophen-3-yl)-imidazo[1,2-a]pyridine, or 2-(3,4-dimethoxy-phenyl)-6-methyl-imidazo[1,2-a]pyridine, is described in more detail in the following examples. The examples are to be considered as being illustrative and representative of the invention, but not as limiting the scope of the present invention.

Pharmaceutically acceptable salts of compounds of formula I can be manufactured readily according to methods known in the art and taking into consideration the nature of the compound to be converted into a salt. Inorganic or organic acids such as, for example, hydrochloric acid, hydrobromic acid, sulfuric acid, nitric acid, phosphoric acid or citric acid, formic acid, fumaric acid, maleic acid, acetic acid, succinic acid, tartaric acid, methanesulfonic acid, p-toluenesulfonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds. Unless stated to the contrary, all of the compounds listed in the examples were prepared and characterized as described.

EXAMPLE 1

7-Chloro-2-(3,4-dimethyl-phenyl)-imidazo[1,2-a]pyridine

To a stirred solution of 2-amino-4-chloro-pyridine (0.39 g, 3.03 mmol) in ethanol (25 ml) was added 3,4-dimethyl-phenacylbromide (0.69 g, 3.03 mmol). The reaction mixture was stirred under reflux conditions for 16 h, poured into sat. NaHCO$_3$ solution (70 ml) and extracted with dichloromethane (70 ml). The combined organic layers were washed with brine (70 ml), dried (MgSO$_4$) and evaporated to give the crude product as a brown solid (0.84 g). Further purification by column chromatography on silica gel (ethyl acetate/toluene 1:9) and crystallization from ethyl acetate/hexane yielded the title compound (0.54 g, 69%) as a pale yellow solid, m.p. 144° C. and MS: m/e=256.2 (M$^+$).

EXAMPLE 2

2-(3,4-Dimethoxy-phenyl)-7-methyl-imidazo[1,2-a]pyridine

The title compound, pale yellow solid, m.p. 163° C. and MS: m/e=268.1 (M$^+$), was prepared in accordance with the general method of example 1 from 2-amino-4-methyl-pyridine and 3,4-dimethoxy-phenacylbromide.

EXAMPLE 3

2-(3,4-Dimethoxy-phenyl)-imidazo[1,2-a]pyridine

The title compound, pale yellow solid, m.p. 96° C. and MS: m/e=254.1 (M$^+$), was prepared in accordance with the general method of example 1 from 2-amino-pyridine and 3,4-dimethoxy-phenacylbromide.

EXAMPLE 4

2-(3,4-Dimethyl-phenyl)-7-methoxy-imidazo[1,2-a]pyridine

The title compound, pale yellow solid, m.p. 175° C. and MS: m/e=252.2 (M$^+$), was prepared in accordance with the general method of example 1 from 2-amino-4-methoxy-pyridine and 3,4-dimethyl-phenacylbromide.

EXAMPLE 5

2-(3,4-Dimethoxy-phenyl)-7-methoxy-imidazo[1,2-a]pyridine

The title compound, pale yellow solid, m.p. 142° C. and MS: m/e=284.1 (M$^+$), was prepared in accordance with the general method of example 1 from 2-amino-4-methoxy-pyridine and 3,4-dimethoxy-phenacylbromide.

EXAMPLE 6

2-(3,4-Dimethyl-phenyl)-imidazo[1,2-a]pyridine hydrochloride

The title compound was obtained in analogy to the method as described in patent application WO 00108021.

EXAMPLE 7

2-(3,4-Dimethyl-phenyl)-7-methyl-imidazo[1,2-a]pyridine

The title compound, solid, MS: m/e=237.0 (M+H$^+$), was obtained in analogy to the general method of example 1.

EXAMPLE 8

2-(3-Bromo-4-fluoro-phenyl)-imidazo[1,2-a]pyridine

In analogy to the method as described in *J. Heterocyclic Chem.* 1988, 25, 129–137, 2-Bromo-1-(3-bromo-4-fluoro-phenyl)-ethanone (89 mg, 0.3 mmol) and 2-Aminopyridine (28 mg, 0.3 mmol) were dissolved in 2 ml of acetone and shaken overnight. The solvent was evaporated and and the residue was dissolved in 1 ml of DMF. The title compound (m/e=292.6, [M+H$^+$]) was isolated from this solution by HPLC chromatography (YMC CombiPrep C18 column 50×20 mm, solvent gradient 10–95% CH$_3$CN in 0.1% TFA(aq) over 6.0 min, λ=230 nm, flow rate 40 ml/min).

EXAMPLE 9

2-(4-Benzyloxy-3-methoxy-phenyl)-imidazo[1,2-a]pyridine

The title compound, MS: m/e=330.9 (M+H$^+$), was prepared in accordance with the general method of example 8 from 1-(4-Benzyloxy-3-methoxy-phenyl)-2-bromo-ethanone.

EXAMPLE 10

2-Indan-5-yl-imidazo[1,2-a]pyridine

The title compound, MS: m/e=234.8 (M+H$^+$), was prepared in accordance with the general method of example 8 from 2-Bromo-1-indan-5-yl-ethanone.

EXAMPLE 11

2-(3-Bromo-phenyl)-imidazo[1,2-a]pyridine

The title compound, MS: m/e=274.5 (M+H$^+$) was prepared in accordance with the general method of example 8 from 2-Bromo-1-(3-bromo-phenyl)-ethanone.

EXAMPLE 12

2-(3-Iodo-phenyl)-imidazo[1,2-a]pyridine

The title compound, MS: m/e=320.7 (M+H$^+$), was prepared in accordance with the general method of example 8 from 2-Iodo-1-(3-bromo-phenyl)-ethanone.

EXAMPLE 13

2-(3-Chloro-phenyl)-imidazo[1,2-a]pyridine

The title compound, MS: m/e=228.5 (M+H$^+$), was prepared in accordance with the general method of example 8 from 2-Chloro-1-(3-bromo-phenyl)-ethanone.

EXAMPLE 14

2-(3-Methyl-phenyl)-imidazo[1,2-a]pyridine

The title compound, MS: m/e=208.8 (M+H$^+$), was prepared in accordance with the general method of example 8 from 2-Bromo-1-m-tolyl-ethanone.

EXAMPLE 15

2-Benzofuran-2-yl-imidazo[1,2-a]pyridine

The title compound, MS: m/e=234.8 (M+H$^+$), was prepared in accordance with the general method of example 8 from 1-Benzofuran-2-yl-2-bromo-ethanone.

EXAMPLE 16

2-Benzo[b]thiophen-3-yl-imidazo[1,2-a]pyridine

The title compound, MS: m/e=250.8 (M+H$^+$), was prepared in accordance with the general method of example 8 from 1-Benzo[b]thiophen-3-yl-2-bromo-ethanone;

EXAMPLE 17

2-(3-Trifluoromethyl-phenyl)-imidazo[1,2-a]pyridine

The title compound, MS: m/e=262.7 (M+H$^+$) was prepared in accordance with the general method of example 8 from 2-Bromo-1-(3-trifluoromethyl-phenyl)-ethanone.

EXAMPLE 18

2-(2,3-Dihydro-benzofuran-5-yl)-imidazo[1,2-a]pyridine

The title compound, MS: m/e=236.8 (M+H$^+$), was prepared in accordance with the general method of example 8 from 2-Bromo-1-(2,3-dihydro-benzofuran-5-yl)-ethanone.

EXAMPLE 19

2-(3-Fluoro-phenyl)-imidazo[1,2-a]pyridine

The title compound, MS: m/e=212.7 (M+H$^+$), was prepared in accordance with the general method of example 8 from 2-Bromo-1-(3-fluoro-phenyl)-ethanone.

EXAMPLE 20

2-(3,4-Dimethyl-phenyl)-7-ethyl-imidazo[1,2-a]pyridine

The title compound, MS: m/e=250.8 (M+H$^+$), was prepared in accordance with the general method of example 8 from 2-Bromo-1-(3,4-dimethyl-phenyl)-ethanone and 4-Ethyl-pyridin-2-ylamine.

EXAMPLE 21

2-(5-Methyl-thiophen-2-yl)-imidazo[1,2-a]pyridine

The title compound, MS: m/e=215.0 (M+H$^+$), was prepared in accordance with the general method of example 8 from 2-Bromo-1-(5-methyl-thiophen-2-yl)-ethanone.

EXAMPLE 22

7-Methyl-2-phenyl-imidazo[1,2-a]pyridine

The title compound, MS: m/e=209.0 (M+H$^+$), was obtained by the method as described in *J. Med. Chem.* 1998, 41(25), 5108–5112.

EXAMPLE 23

2-(4-Methyl-phenyl)-imidazo[1,2-a]pyridine

The title compound, MS: m/e=209.2 (M+H$^+$), was obtained by the method as described in patent application EP 0 533 058.

EXAMPLE 24

2-(2,5-Dimethyl-thiophen-3-yl)-imidazo[1,2-a]pyridine

The title compound, MS: m/e=229.0 (M+H$^+$), was prepared in accordance with the general method of example 8 from 2-bromo-1-(2,5-dimethyl-thiophen-3-yl)-ethanone.

EXAMPLE 25

2-(3-Methoxy-phenyl)-imidazo[1,2-a]pyridine

The title compound, MS: m/e=224.8 (M+H$^+$), was prepared in accordance with the general method of example 8 from 2-bromo-1-(3-methoxy-phenyl)-ethanone.

EXAMPLE 26

2-(3,4-Dimethoxy-phenyl)-6-methyl-imidazo[1,2-a]pyridine

The title compound, MS: m/e=269.2 (M+H$^+$), was prepared in accordance with the general method of example 8 from 5-methyl-pyridin-2-ylamine and 2-bromo-1-(3,4-dimethoxy-phenyl)-ethanone.

EXAMPLE 27

2-(2,3-Dihydro-benzo[1,4]dioxin-6-yl)-imidazo[1,2-a]pyridine

The title compound, MS: m/e=253.0 (M+H$^+$), was prepared in accordance with the general method of example 8 from 2-bromo-1-(2,3-dihydro-benzo[1,4]dioxin-6-yl)-ethanone.

EXAMPLE 28

6-Methyl-2-(4-methyl-phenyl)-imidazo[1,2-a]pyridine

The title compound, MS: m/e=223.0 (M+H$^+$), was obtained by the method as described in patent application EP 1 038 875.

EXAMPLE 29

2-(3-Nitro-phenyl)-imidazo[1,2-a]pyridine

The title compound, MS: m/e=240.2 (M+H$^+$), was prepared in accordance with the general method of example 8 from 2-bromo-1-(3-nitro-phenyl)-ethanone.

EXAMPLE A

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound selected from the group consisting of
7-Chloro-2-(3,4-dimethyl-phenyl)-imidazo[1,2-a]pyridine,
2-(3,4-dimethoxy-phenyl)-imidazo[1,2-a]pyridine,
2-(3,4-dimethyl-phenyl)-7-methoxy-imidazo[1,2-a]pyridine,
2-(3,4-dimethoxy-phenyl)-7-methoxy-imidazo[1,2-a]pyridine,
2-(3,4-dimethyl-phenyl)-7-methyl-imidazo[1,2-a]pyridine,
2-(3-bromo-4-fluoro-phenyl)-imidazo[1,2-a]pyridine,
2-(4-benzyloxy-3-methoxy-phenyl)-imidazo[1,2-a]pyridine,
2-indan-5-yl-imidazo[1,2-a]pyridine,
2-(3-bromo-phenyl)-imidazo[1,2-a]pyridine,
2-(3-iodo-phenyl)-imidazo[1,2-a]pyridine,
2-(3-methyl-phenyl)-imidazo[1,2-a]pyridine,
2-benzo[b]thiophen-3-yl-imidazo[1,2-a]pyridine,
2-(3-trifluoromethyl-phenyl)-imidazo[1,2-a]pyridine,
2-(2,3-dihydro-benzofuran-5-yl)-imidazo[1,2-a]pyridine,
2-(3-fluoro-phenyl)-imidazo[1,2-a]pyridine,
2-(3,4-dimethyl-phenyl)-7-ethyl-imidazo[1,2-a]pyridine,
2-(5-methyl-thiophen-2-yl)-imidazo[1,2-a]pyridine,
2-(2,5-dimethyl-thiophen-3-yl)-imidazo[1,2-a]pyridine, and
2-(3,4-dimethoxy-phenyl)-6-methyl-imidazo[1,2-a]pyridine.

2. A pharmaceutical composition comprising a therapeutically effective amount of at least one compound, or a pharmaceutically acceptable salt thereof, selected from the group consisting of 7-chloro-2-(3,4-dimethyl-phenyl)-imidazo[1,2-a]pyridine, 2-(3,4-dimethoxy-phenyl)-imidazo[1,2-a]pyridine, 2-(3,4-dimethyl-phenyl)-7-methoxy-imidazo[1,2-a]pyridine, 2-(3,4-dimethoxy-phenyl)-7-methoxy-imidazo[1,2-a]pyridine, 2-(3,4-dimethyl-phenyl)-7-methyl-imidazo[1,2-a]pyridine, 2-(3-bromo-4-fluoro-phenyl)-imidazo[1,2-a]pyridine, 2-(4-benzyloxy-3-methoxy-phenyl)-imidazo[1,2-a]pyridine, 2-indan-5-yl-imidazo[1,2-a]pyridine, 2-(3-bromo-phenyl)-imidazo[1,2-a]pyridine, 2-(3-iodo-phenyl)-imidazo[1,2-a]pyridine, 2-(3-methyl-phenyl)-imidazo[1,2-a]pyridine, 2-benzo[b]thiophen-3-yl-imidazo[1,2-a]pyridine, 2-(3-trifluoromethyl-phenyl)-imidazo[1,2-a]pyridine, 2-(2,3-dihydro-benzofuran-5-yl)-imidazo[1,2-a]pyridine, 2-(3-fluoro-phenyl)-imidazo[1,2-a]pyridine, 2-(3,4-dimethyl-phenyl)-7-ethyl-imidazo[1,2-a]pyridine, 2-(5-methyl-thiophen-2-yl)-imidazo[1,2-a]pyridine, 2-(2,5-dimethyl-thiophen-3-yl)-imidazo[1,2-a]pyridine and 2-(3,4-dimethoxy-phenyl)-6-methyl-imidazo[1,2-a]pyridine; and a pharmaceutically acceptable carrier.

3. A method of treatment or prevention of a mGluR5 receptor mediated disease comprising administering, to a person in need of such treatment, a therapeutically effective amount at least one compound, or a pharmaceutically acceptable salt thereof, selected from the group consisting of 7-chloro -2-(3,4-dimethyl-phenyl)-imidazol[1,2-a]pyridine, 2-(3,4-dimethoxy-phenyl)-imidazo[1,2-a]pyridine, 2-(3,4-dimethyl-phenyl)-7-methoxy-imidazo[1,2-a]pyridine, 2-(3, 4-dimethoxy-phenyl)-7-methoxy-imidazo[1,2-a]pyridine, 2-(3,4-dimethyl-phenyl)-7-methyl-imidazo[1,2-a]pyridine, 2-(3-bromo-4-fluoro-phenyl)-imidazo[1,2-a]pyridine, 2-(4-benzyloxy-3-methoxy-phenyl)-imidazo[1,2-a]pyridine, 2-indan-5-yl-imidazo[1,2-a ]pyridine, 2-(3-bromo-phenyl)-imidazo[1,2-a]pyridine, 2-(3-iodo-phenyl)-imidazo[1,2-a]pyridine, 2-(3-methyl-phenyl)-imidazo[1,2-a]pyridine, 2-benzo[b]thiophen-3-yl-imidazo[1,2-a]pyridine, 2-(3-trifluoromethyl-phenyl)-imidazo[1,2-a]pyridine, 2-(2,3-dihydro-benzofuran-5-yl) -imidazo[1,2-a]pyridine, 2-(3-fluoro-phenyl )-imidazo[1,2-a]pyridine, 2-(3,4-dimethyl-phenyl) -7-ethyl-imidazo[1,2-a]pyridine, 2-(5-methyl-thiophen-2-yl)-imidazo[1,2-a]pyridine, 2-(2,5-dimethyl-thiophen-3-yl )-imidazo[1,2-a]pyridine, and 2-(3,4-dimethoxy-phenyl )-6-methyl -imidazo[1,2-a]pyridine.

4. The method according to claim 3 wherein the mGluR5 mediated disease is acute and/or chronic pain.

5. The method according to claim 3, wherein the mGluR5 mediated disease is Alzheimer's disease.

6. The method according to claim 3 wherein the mGluR5 mediated disease is Parkinson's disease.

7. The method according to claim 3 wherein the mGluR5 mediated disease is anxiety and depression.

* * * * *